United States Patent [19]

Schneider

[11] 3,948,256

[45] Apr. 6, 1976

[54] OSTOMY APPLIANCE DEVICE
[76] Inventor: George A. Schneider, 1802 W. Minnehaha, St. Paul, Minn. 55104
[22] Filed: Apr. 16, 1975
[21] Appl. No.: 568,594

[52] U.S. Cl. .............................................. 128/283
[51] Int. Cl.² ........................ A61M 3/00; A61F 5/44
[58] Field of Search ..................................... 128/283

[56] References Cited
UNITED STATES PATENTS

| | | | |
|---|---|---|---|
| 2,684,676 | 7/1954 | Perry | 128/283 |
| 2,902,036 | 9/1959 | Perry | 128/283 |
| 3,043,306 | 7/1962 | Hergatt et al. | 128/283 |
| 3,481,336 | 12/1969 | Ipson | 128/283 |
| 3,672,370 | 6/1972 | Marsan | 128/283 |
| 3,822,704 | 7/1974 | Nolan | 128/283 |

*Primary Examiner*—Aldrich F. Medbery
*Attorney, Agent, or Firm*—Jacobson and Johnson

[57] ABSTRACT

A ring made of stiff, smooth material passes through concentric openings on a pair of separable plate members to accommodate the stoma to allow discharge into a disposable container attached to one of the plates. Annular washers around the plate openings and the ring seal against leakage, permit the plates to be quickly and easily separated and permit the appliance to be easily disassembled, if necessary, for cleaning.

8 Claims, 2 Drawing Figures

U.S. Patent    April 6, 1976    3,948,256
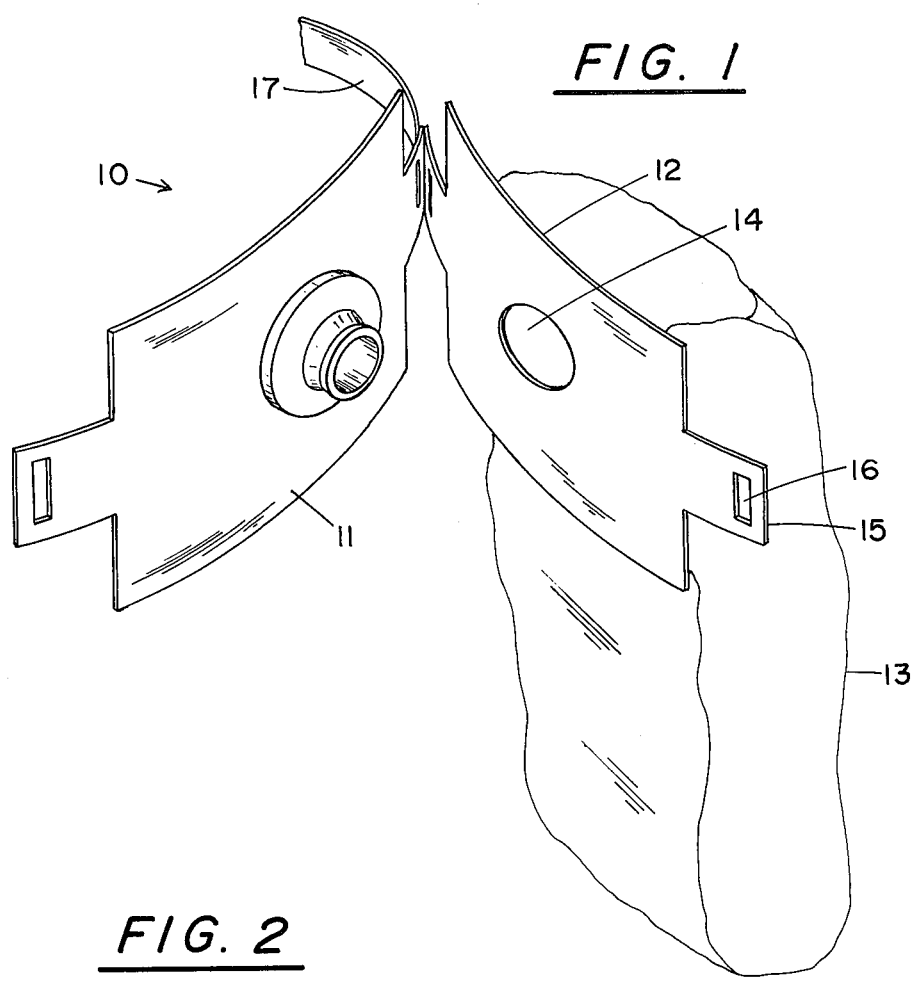
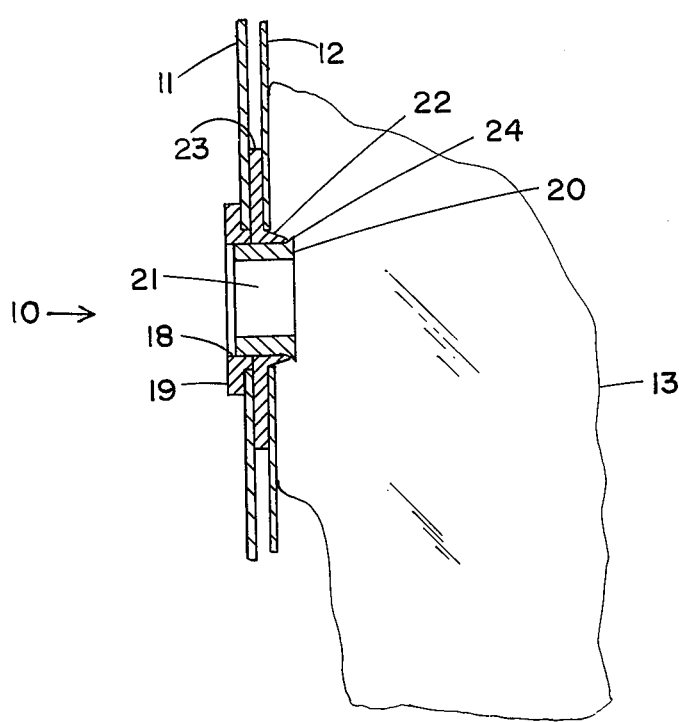

OSTOMY APPLIANCE DEVICE

BACKGROUND OF THE INVENTION

Field of the Invention

This invention relates to devices for gathering the waste material from persons who have undergone colostomy or ileostomy operations or the like. Although henceforth the invention will be described as a colostomy appliance, it should be understood that the features and advantages are equally applicable to other ostomy devices.

There are a large variety of portable colostomy appliances available today. A number of patented devices are illustrated and described in the following U.S. Pat. Nos. 2,902,036; 2,721,553; 2,808,830; 3,283,757; 3,043,306; 2,675,002; 3,789,846; 3,612,053; 2,874,697; 2,692,597. Basically, the design of all appliances is directed toward providing a means for retaining a disposable container in communication with the stoma opening to collect the waste material while at the same time avoiding any leakage outside of the container while the container is being worn.

As any colostomate realizes, the greatest problems encountered with appliances that are available today are the physical discomfort, the limit they place on the mobility of the colostomate who is always fearful of the security of the appliance and is concerned about moving about which could cause it to leak, the difficulty of cleaning out the device each time there has been a discharge, and the need for quickly and temporarily opening the appliance for release of gas or for other reasons. The instant invention provides these features while at the same time provides the basic design requirements described above and permits the disposable waste container to be easily and quickly removed and replaced with a clean fresh one.

SUMMARY OF THE INVENTION

An inner plate which provides stability for the appliance is held against the body of the user by a layer of adhesive and by connection to a belt worn by the user. The inner plate has a round aperture which is aligned with the stoma and this aperture has an annular sealing washer around it and a ring of stiff, smooth material is mounted within the washer opening to accommodate the stoma. The ring is sealed against leakage beyond the inner plate by a further washer around the outside surface of the ring and which has a flange adjacent the outside surface of the inner plate. An outer plate, similar in construction to the inner plate, has an opening through which the outer sealing washer and the ring pass into a disposable container which is adhesively attached to the outer surface of the outer plate and has an opening aligned with the opening in the outer plate. The outer plate is held in position by a detachable connection to a belt worn by the user. For disposal of any of the waste material accumulated in the container, the container merely has to be stripped off the outer plate and replaced with a clean fresh one. The appliance can be momentarily opened merely by detaching the outer plate from the belt connection and lifting it away from the ring and the outer sealing washer. Similarly, the appliance can be readily cleaned by opening the outer plate to permit easy access to the ring and the sealing washers. The outer sealing washer and the ring can be quickly removed for cleaning or replacement, if necessary, and for access to the stoma, if desired. Generally, the inner plate need not be disturbed so that there is no need to repeatedly peel away the adhesive from the skin. From time to time, of course, it is necessary to lift the inner plate off the skin for medicinal reasons but it only has to be done occasionally and does not have to be done each time there has been a discharge or for irrigating or for other periodic need of the colostomate.

BRIEF DESCRIPTION OF THE DRAWING

FIG. 1 is a perspective view of an embodiment of the invention as it appears when opened; and FIG. 2 is a side elevational sectional view showing an embodiment of the invention as it appears in normal use.

DESCRIPTION OF THE PREFERRED EMBODIMENTS

The ostomy appliance 10 has an inner plate 11 and an outer plate 12 which are virtually identical in construction and are made out of a thin sheet of relatively stiff, yet somewhat pliable material. The inner plate provides support for the appliance at the body of the wearer and the outer plate provides the support for the disposable waste container 13 which is adhesively attached thereto. Therefore, these plates must have sufficient rigidity to perform these functions but at the same time, of course, must have some amount of pliability to allow them to conform somewhat to the shape of the wearer's body and to have some amount of flexibility while the wearer is moving. Each of the plates has a circular opening 14 and each has an extension 15 at each side containing a slot 16 for releasably engaging a belt, illustrated partially at 17, which encircles the body of the user. Although a simple slot construction is illustrated, no limitation thereto is intended since it should be understood that there are a number of ways in which the plates can be releasably attached to a belt worn by the user.

Mounted within the opening 14 of the inner plate 11 is an annular resilient washer 18. While the illustrated embodiment shows the washer 18 as having a rearwardly disposed shoulder 19 which assists in holding the washer in place in the inner plate 11, the shoulder 19 is not necessary and furthermore it is preferred that the shoulder be quite thin so that the inner surface of the inner plate 11 rests close against the body of the wearer. Preferably, the inner surface of the inner plate 11 has a thin layer of adhesive to assist in holding the inner plate firmly against the body of the wearer during use. The inner plate 11 is is also held in place by a releasable attachment to the belt 17 as described earlier. Located within the annular opening of washer 18 is an annular ring 20 which extends outward beyond the inner plate 11. The ring 20 should be made of a stiff, smooth material, preferably a plastic material which is inert to any of the waste materials which might be discharged from the colostomate. The annular opening 21 of ring 20 accommodates the colostomate's stoma, not shown. Beyond the inner plate 11 around the annular ring 20 is a further annular washer 22 made of a rubbery or resilient material. Washer 22 extends forward about the same length of the ring 20 and rearwardly, adjacent the outer surface of inner plate 11, has a flange portion 23. The flange serves a twofold purpose. One is to assist in ensuring a good seal against any leakage and the other is to provide some cushioning effect between the outer plate 12, which carries the disposable container, and the remainder of the appliance including the inner plate 11. With the resiliency and flexibility of the washers 18 and 22, including the flange portion 23, the appliance assembly is securely held together and yet has a great deal of resiliency or flexibility so that in normal use when being carried by the wearer it is less likely to be bothersome to the wearer or to inhibit the wearer in his movement which otherwise is the case with the more traditional colostomy appliances where rigid construction causes the wearer to be concerned with possible breakage or tearing when the discharge bag becomes even partly filled. The outer end of the ring 20 is illustrated as having a lip 24 to keep washer 22 from moving forward off ring 20. While it is preferred that the inner washer 18 and the outer washer 22 can be separate, they could be formed as one unitary body.

In normal use, as illustrated in FIG. 2, the opening 14 of the outer plate 12 is concentric with the opening of the inner plate 11 and the outer plate 12 is located so that the extension of the ring 20 and the sealing washer 22 extend through the opening 14 into the container 13 through an opening in the container which is aligned with opening 14 in the outer plate 12. Preferably the container 13 is a flexible plastic bag which is attached to the outer plate 12 by adhesive and can be readily removed and replaced by stripping it off the outer plate 12 and replacing it with a new clean bag as needed. The opening 14 in the outer plate 12 is sealed closed at its periphery by washer 22 to prevent any leakage from occurring in that area. The outer plate 12 is held in place by attachment to a belt 17 worn by the user in a fashion as described earlier. A separate belt can be used for each plate or both plates can be held in place by the same belt. It is further contemplated that a set of two belts can be used to hold the appliance in place more firmly during use. The two belts would be worn one above the other and would require two slots, one above the other, on each of the plates for making the detachable connection to the respective belts.

When the appliance is attached and in normal use by the wearer, as illustrated in FIG. 2, if for example the container becomes full, all the wearer has to do is strip the container from the outer plate 12, dispose of it and replace it with a new container without disturbing the stoma or the attachment of the appliance to the skin or or body of the wearer. Ordinarily the wearer at the same time will want to clean up any droppings in the appliance and this can be done easily merely by detaching the outer plate from its belt connection and swinging it open, somewhat in a fashion as illustrated in FIG. 1, and reaching in with a suitable cleaning paper to wipeoff the stoma, the areas around the openings and the ring 20 and the washer 22. Further, the ring 20 and the outer washer 22 can be easily slipped out and cleaned and while they are removed the user has access to the inner washer 18 and further access to the stoma for cleaning, if necessary. From time to time, of course, for medicinal reasons the inner plate 11 may have to be replaced by stripping it off the skin of the user and replaced with a new inner plate or with the same inner plate after the area around the stoma has been suitably cleaned. This only has to be done occasionally and does not have to be done each time the appliance is to be cleaned after a discharge. To release gas, the outer plate 12 need only be temporarily released from the belt 17 and opened momentarily and then reclosed. It should be noted that the plates can be releasably attached to the belt at both sides or they can be permanently attached to the belt at one side and releasably attached at the other side. Preferably both plates should be releasably attached to the belt at both sides so that the appliance is independent of the belt. The embodiment described is adaptable for use with appliance belts that are presently available and also with a variety of different disposable waste containers that are available on the market today. In other words, it is not necessary that a new type of belt or disposable container be designed and produced to be used with the appliance of the instant invention.

I claim:

1. An ostomy appliance device comprising: an inner plate having a round aperture and means for releasable attachment to a belt worn by the wearer; a first resilient annular sealing washer mounted in the inner plate aperture; a ring of stiff smooth-surfaced material sealably engaged in the opening of said first annular washer, said ring extending beyond said inner plate and having an opening for receiving the stoma; a second resilient annular sealing washer around said ring beyond the inner plate, said second washer having an annular resilient flange adjacent the outer surface of the inner plate; and an outer plate having an opening for receiving the extension of said ring and said second washer, said second washer releasably sealing closed the periphery of the outer plate opening when engaged therewith, said outer plate having means for releasable attachment to a belt worn by the wearer.

2. The invention as set forth in claim 1 wherein said second plate is substantially coextensive with said inner plate and both plates have some limited amount of pliability.

3. The invention as set forth in claim 1 wherein said inner plate has a layer of adhesive on its inner surface for attaching the inner plate to the wearer's body.

4. The invention as set forth in claim 1 further including a container releasably attached to said outer plate having an opening coextensive with the opening in said outer plate, the periphery of said container opening being sealed closed around the outer plate opening.

5. The invention as set forth in claim 1 wherein said outer plate is selectively engaged with and disengaged from said second washer as desired to respectively close together and separate the inner and outer plates.

6. The invention as set forth in claim 1 wherein said ring is removably engaged with said first annular washer.

7. The invention as set forth in claim 6 wherein said ring is removably engaged with said second annular washer.

8. The invention as set forth in claim 6 wherein said first and second washers are one unitary body.

* * * * *